United States Patent [19]

Burrington et al.

[11] Patent Number: 4,782,173

[45] Date of Patent: Nov. 1, 1988

[54] SYNTHESIS OF METHIONINE HYDROXY ANALOG OR DERIVATIVE, AND ESTERS THEREOF; SYNTHESIS OF 1-ACYLOXY-4-HYDROCARBYLTHIOPROPENE, AND PRODUCTS

[75] Inventors: James D. Burrington, South Euclid; Mark C. Cesa, Richmond Heights, both of Ohio

[73] Assignee: The Standard Oil Company, Cleveland, Ohio

[21] Appl. No.: 520,042

[22] Filed: Aug. 3, 1983

[51] Int. Cl.$^4$ .................. C07C 153/09; C07C 149/20
[52] U.S. Cl. ..................................... 558/255; 560/262; 560/264; 562/581
[58] Field of Search ............... 560/152, 238, 262, 232, 560/114; 562/581; 260/455 R, 399; 558/255

[56] References Cited

U.S. PATENT DOCUMENTS

| | | | |
|---|---|---|---|
| 2,021,698 | 1/1933 | Perkins | 560/238 |
| 2,768,968 | 10/1956 | Reppe et al. | 560/233 |
| 3,437,676 | 4/1969 | von Kutepow et al. | 560/233 X |
| 3,793,369 | 2/1974 | Hara et al. | 560/233 |
| 4,120,885 | 10/1978 | Diamond | 424/301 |
| 4,323,517 | 4/1982 | Optiz et al. | 260/455 R |
| 4,377,708 | 3/1983 | Morris | 560/232 X |
| 4,399,302 | 8/1983 | Kleeman et al. | 560/238 |

FOREIGN PATENT DOCUMENTS

| | | | |
|---|---|---|---|
| 2500448 | 8/1982 | France . | |
| 21057 | 9/1968 | Japan | 560/238 |
| 2044755 | 10/1980 | United Kingdom | 560/152 |

OTHER PUBLICATIONS

*Angew. Chem. Int. Ed. Engl.,* vol. 18, No. 10 (1979), p. 797 Kleeman et al.
Conant, *The Chemistry of Organic Compounds,* pp. 264–265, The Macmillan Co., NY, 1939, QD 251C67.
March, Advanced Organic Chemistry, Reactions, Mechanisms, and Structure, Second edition, 1977, pp. 736–737.

*Primary Examiner*—Michael L. Shippen
*Attorney, Agent, or Firm*—C. S. Lynch; D. J. Untener; L. W. Evans

[57] ABSTRACT

Discloses (1) reacting a 3-(hydrocarbylthio) propionaldehyde with a compound

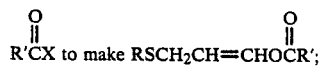

(2) reacting latter compound with CO and R"YH where y is O or S to make

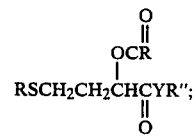

(3) hydrolyzing this compound; (4) certain new 1-acyloxy-3-methylthiopropenes and (5) the methyl ester of 2-acetoxy-4-(methylthio)thiobutanoic acid.

3 Claims, No Drawings

SYNTHESIS OF METHIONINE HYDROXY ANALOG OR DERIVATIVE, AND ESTERS THEREOF; SYNTHESIS OF 1-ACYLOXY-4-HYDROCARBYLTHIOPROPENE, AND PRODUCTS

In one aspect this invention relates to making methionine hydroxy analog or derivative, and esters thereof. Specifically, the methionine hydroxy analog or derivative has the formula,

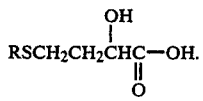

In this formula where R is methyl, the compound is known as methionine hydroxy analog, also known as 4-methylthio-2-hydroxybutanoic acid. In this application, the "derivative" means a compound of the foregoing formula where R is other than methyl. In one aspect there is disclosed and claimed a method of making such compound in a three step process which starts with a 3-(hydrocarbylthio)propionaldehyde. In another aspect of the invention there is disclosed and claimed a method of making esters of methionine hydroxy analog or its derivative beginning with a 1-acyloxy-3-hydrocarbylthiopropene.

In a still further aspect of the invention a new method of making a 1-acyloxy-3-hydrocarbylthiopropene from a 3-(hydrocarbylthio)propionaldehyde is disclosed and claimed, as are certain new 1-acyloxy-3-hydrocarbylthiopropenes per se.

The now most important product of the present invention is the hydroxy analog of methionine. It is a well known and important feed supplement for various animal feeds. It is generally commercially made by a 4-step process in which acrolein is reacted with methane thiol to produce 3-(methylthio)propionaldehyde; thereafter the 3-(methylthio)propionaldehyde is reacted with HCN to produce 2-hydroxy-4-methylthiobutyronitrile. This compound is then reacted with water to produce 2-hydroxy-4-methylthiobutyramide, which in turn is reacted with water and sulfuric acid to produce the methionine hydroxy analog.

This prior art process is disadvantageous because of the use of HCN which requires costly handling because of possible safety hazards. In addition, production of unwanted by-product ammonium sulfate is also a problem. Stoichiometric amounts of sulfuric acid are also required, an added cost and a corrosion problem.

It is one object of the present invention to provide a new process for making methionine hydroxy analog without using HCN as a reactant and without producing by-product ammonium sulfate. It is a further object to provide a process for making compounds of the formula

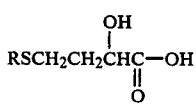

including methionine hydroxy analog) wherein R is a hydrocarbyl group containing 1-30 carbon atoms but not containing any ethylenic or acetylenic unsaturation.

It is a still further object to provide a useful intermediate for preparing said compound of the formula

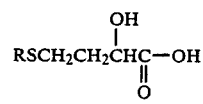

by reacting a 3-(hydrocarbylthio)propionaldehyde with a suitable reagent to produce a compound

1-acyloxy-3-hydrocarbylthiopropene.

Other objects, as well as aspects, advantages and features, of the present invention will become apparent from a study of the specification and the appended claims. The foregoing and other objects are fulfilled in accordance with the present invention described more fully hereafter.

According to one aspect of the present invention there is provided a process for producing a compound which is hydrolyzable to produce methionine hydroxy analog or a derivative thereof which comprises (a) reacting a 3-(hydrocarbylthio)propionaldehyde $RSCH_2CH_2CHO$, with a reactant of the formula

to produce a compound

1-acyloxy-3-hydrocarbylthiopropene, (b) intimately contacting and reacting said compound,

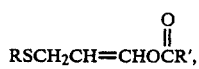

with CO and a reactant of the formula R″YH to produce a compound,

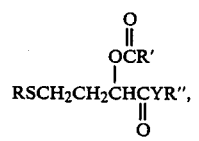

which is hydrolyzable to produce said methionine hydroxy analog or derivative,

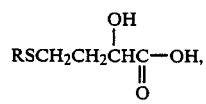

where Y is O or S; X is

F, Cl, Br, I, O-2-propenyl, O-1-propenyl or O-vinyl; R is $C_1$ to $C_{30}$ hydrocarbyl, R' is H or $C_1$ to $C_{30}$ hydrocarbyl and each R' in

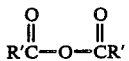

may be the same or different, but only one R' can be H; R" is H or $C_1$ to $C_{30}$ hydrocarbyl when Y is O and is $C_1$ to $C_{30}$ hydrocarbyl when Y is S; and wherein R, R' and R" contain no ethylenic or acetylenic unsaturation, and wherein R' is not H when X is halogen or

Usually in such a process R, R' and R" are limited to a maximum of 10 carbon atoms, all of which are members of an open chain alkyl group.

In another aspect of the invention there is provided a process for making an enol ester having the formula

comprising reacting a 3-(hydrocarbylthio)propionaldehyde with a reactant of the formula

wherein X is

F, Cl, Br, I, O-2-propenyl, O-1-propenyl, or O-vinyl; R is $C_1$ to $C_{30}$ hydrocarbyl; R' is H or $C_1$ to $C_{30}$ hydrocarbyl, and each R' in

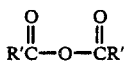

may be the same or different; and wherein R and R' contain no ethylenic or acetylenic unsaturation, and wherein R' is not H when X is halogen or

Usually in such process each of R and R' are limited to a maximum of 10 carbon atoms, all of which are members of an open chain alkyl group.

In still another aspect of the invention there is provided a process which comprises making a compound,

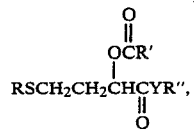

by intimately contacting and reacting an enol ester of the formula

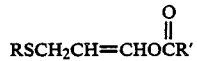

with CO and a reactant of the formula R"YH wherein Y is O or S; R is $C_1$ to $C_{30}$ hydrocarbyl; R" is H or $C_1$ to $C_{30}$ hydrocarbyl when Y is O and is $C_1$ to $C_{30}$ hydrocarbyl when Y is S; and wherein R, R', and R" contain no ethylenic or acetylenic unsaturation. Usually in such process each of R and R' are limited to a maximum of 10 carbon atoms, all of which are members of an open chain alkyl group.

In a further aspect of the invention, we have provided a new compound, 2-acetoxy-4-(methylthio)thiobutanoic acid, methyl ester.

In yet another aspect of the present invention we have provided certain new compounds, 1-acyloxy-3-methylthiopropenes.

The objects of the present invention are realized in accordance with our invention wherein methionine hydroxy analog or a derivative thereof is made through the hydrocarboxylation of the enol acylate of a 3-(hydrocarbylthio) propionaldehyde rather than by the route of hydrocyanation of such an aldehyde, in accordance with the following principal reactions:

Reaction (1):

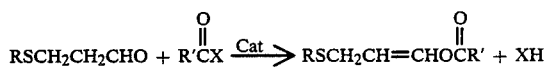

Reaction (2):

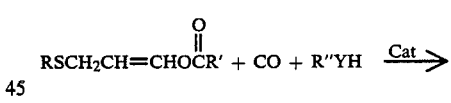

Reaction (3):

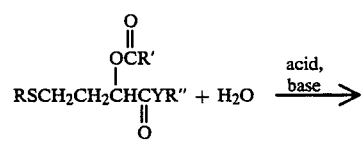

In the foregoing reactions the various R groups and X are as before stated.

It is advantageous that the starting material in Reaction (1), the 3-(hydrocarbylthio)propionaldehyde is easily obtained from the relatively inexpensive and widely available acrolein, by reaction of acrolein with a hycrocarbyl mercaptan having the formula RSH. Such reactions are shown, for instance, in U.S. Pat. Nos. 2,676,190; 2,584,496; 2,564,105; 2,557,913; 2,512,677; 2,485,236; 2,776,996 and 2,626,282.

Reaction (1) is carried out catalytically, and a variety of catalysts can be used. For example, the catalysts can be any Lewis acid or base or Bronsted acid or base, or combinations of these, including:

(a) $H_hX_x$, where X=F, Cl, Br, I, CN, SCN, NCS, O, $SO_4$, $NO_3$, $PO_4$, $RSO_3$,

OCR, $ClO_4$, $ClO_3$, ClO, $HCO_3$, $CO_3$, S, Se, $BF_4$, $BCl_4$, $B(C_6H_5)_4$, $PF_6$, $PCl_6$; h=1-3, x=1-3;

(b) a heteropolyacid or acidic or basic organic resin, or any metal oxide;
(c) $BX_3$ (X as above), $PX_5$, $SnX_2$, $CuX_2$, $ZnX_2$;
(d) $NR_3$, $PR_3$, $AsR_3$, $BiR_3$;
(e) $M_m(OH)_nO_x$, where M=Li, Na, K, Rb, Cs, Be, Mg, Ca, Fe, Co, Rh, Ir, Ni, Pd, Pt, Ru, Mn, Re, Cr, Mo, W, or combination of the above; m=1-4, n=1-8; x=0-4, wherein n+x≧1;
(f) $M_mX_x$ with M, m, X and x as defined above;

wherein R is H or any hydrocarbyl, usually with 1-30 C atoms, more often 1-10 C atoms, and wherein the R's in any particular compound can be the same or different.

The catalysts may be used in a homogeneous mode or may be supported on or incorporated into a heterogeneous-mode support or polymer.

A by-product of Reaction (1) can be the 1,1 diacyloxy compound, $RSCH_2CH_2CH(O_2CR')_2$, and acid catalysts favor its formation. Therefore, even though the diester can be recycled in a continuous process by hydrolysis to the aldehyde and the R' acid $R'CO_2H$, this involves an extra step. We therefore now prefer to use basic catalysts. Of the basic catalysts we now prefer KOAc, NaOAc or other alkali metal acetates, alkali metal hydroxides, and amines.

The reaction can be carried out in batch operation or continuously in the homogeneous or heterogeneous modes. If in the liquid phase, the catalyst can be dissolved in the reactants or can be present as a liquid or a solid. If the reactants are gaseous, the catalyst can be in the form of a liquid or a solid.

The concentrations of reactants and catalysts can vary widely. The ratio of the acylating agent

R'CX to the aldehyde can be 0.1 to 100, usually 0.5 to 10, more usually 1.0 to 5, but most often is 1.0 to 1.5 on a molar basis. The amount of catalyst in the reaction system in batch operation can also vary widely. For convenience, the amount of catalyst can be between 0.01 to 100 mole-percent, usually 0.1 to 10 mole-percent based on the aldehyde reactant.

The reaction system can include a solvent, although this is not necessary. Examples of suitable solvents, which should be inert in the reaction mixtures, are carbon tetrachloride, dimethyl formamide, and toluene. Any amount of solvent can be used, although for convenience the reactant should be present in amounts of at least 0.01 weight percent in the solvent. An especially useful solvent is diethylene glycol dimethyl ether, or 2,2'-dimethoxydiethyl ether since use of this solvent minimizes or eliminates formation of the 1,1-diester, especially when using a basic catalyst. This and any other inert solvent that dissolves all reactants have this effect.

The reaction time can vary widely. Suitable reaction times are 0.1 to 50 hours, preferably 0.1 to 3 hours. The reaction temperature can also vary widely. Usual reaction temperatures are 80° to 130° C., more usually 90° to 110° C.

After the reaction has terminated, the gross reaction product is separated and recovered in a conventional manner. For example, 1-acetoxy-3-methylthiopropene can be recovered from a liquid reaction system by vacuum distillation.

Hydrocarboxylation of vinyl acetate with $H_2O$ is known. See U.S. Pat. No. 4,377,708. In the inventive process carboxylation is carried out on a sulfur-containing enol ester using water, alcohols, or hydrocarbyl sulfides, etc. In accordance with this aspect of the invention, it has been found that the sulfur in the sulfur-containing enol ester does not poison the effective metal compound catalyst as discussed below, even though sulfur is a known poison in other types of systems using such catalysts.

Hydrocarboxylation Reaction (2) is carried out catalytically, discussed in more detail hereafter. Reaction (2) can also be carried out continuously or in batch operation in the liquid or vapor phases. Usually the reaction is carried out in batch operation in a solvent under pressure.

The reactant concentrations can vary widely and are not critical. For convenience, the ratio of the hydrocarboxylation reactant (R'YH) to the enol ester should be no greater than 10/1 on a molar basis. The amount of carbon monoxide can vary widely, but it is preferred to carry out the reaction under a carbon monoxide pressure of 15 to 3500 psig, preferably 500 to 2500 psig. The amount of catalyst can also vary widely. Most conveniently, the amount of catalyst is between 0.01 and 100 mole-percent based on the enol ester, more usually 0.1 to 10 mole-percent.

Usually, the reaction is carried out with a solvent. The solvent should be inert under the reaction conditions and preferably dissolves the active catalyst species. Suitable solvents found to date are tetrahydrofuran, benzene, $CH_3CN$ and $CH_2Cl_2$ and $CH_3Cl$. The now preferred solvent is tetrahydrofuran, particularly when using $(\phi_3P)_2PdCl_2$ catalyst, or other palladuim compounds. Usually, the amount of solvent in the system will be such that the enol ester concentration is at least about 0.01 weight percent in the solution, but not over 70 weight percent.

The reaction is normally carried out at a temperature of 0° to 250° C., preferably 20° to 150° C. However, the reaction temperature can be below or above this if desired. Reaction times on the order of 0.1 to 250 hours can be employed, with reaction times on the order of 2 to 100 hours being more convenient.

While a wide variety of complexes of transition metals are known as catalysts for the hydrocarboxylation of alkenes (See, for instance, 1) Pino, P., Piacenti, F., in *Organic Synthesis via Metal Carbonyls*, Volume 2, Wender, I., Pino, P., eds., Wiley, New York, 1977, pp. 233-296; 2) Falbe, J., *New Syntheses with Carbon Monox-* ide, New York, Springer Verlag, Chapter 3 and 5; 3) Forster, D.; Hershman, A.; Morris, D. E., *Catal. Rev. -Sci. Eng.* 23, 89–105 (1981); 4) Parshall, G. W., *Catal. Rev. Sci. - Eng.*, 23, 107–124 (1981); 5) Bittler, J, v. Kutepow, N., Neubauer, D., Reis, H., *Angew. Chem. Intl. Ed. Eng.*, 7, 329–335(1968),) many such catalysts are poisoned by sulfur compounds. Indeed, we have found that most such catalysts tried are not effective in reaction (2) herein, as will be seen from the specific examples. We have discovered that palladium coordination complexes are remarkably effective when considered in the light of experience with other known transition metal catalyst complexes for hydrocarboxylation of alkenes, or for hydroformylation for enol ethers or enol acetates (U.S. Pat. No. 3,888,880; B. Fell, M. Barl, *J. Mol. Catal.*, 1977, 2, 301–6; Tinker, Harold B. (Monsanto) Ger. Offen. No. 2,623,673; U.S. Pat. No. 4,072,709). Especially useful Pd complexes are $(\phi_3P)_2PdCl_2$ and $(\phi_3P)_4Pd$ with HCl as a co-catalyst. When $(\phi_3P)_2PdCl_2$ is the catalyst, the now preferred reaction solvent is tetrahydrofuran.

Once a reaction is completed, the 2-acyloxy-4-(hydrocarbylthio)butanoic acid (or thioacid) or ester product can be recovered from the reaction system in a conventional manner, such as for example, by vacuum distillation.

The third step in the inventive process is the hydrolysis of the 2-acyloxy-4-(hydrocarbylthio)butanoic acid or thioacid or ester.

Reaction (3) is a conventional hydrolysis reaction. It is catalyzed by any dilute aqueous acid or base. Suitable acids or bases are HCl, $H_2SO_4$, $HNO_3$, $H_3PO_4$, acetic acid, KOH, NaOH and $NH_4OH$. The reaction is conveniently carried out at temperatures at above 0° C. to 120° C., more usually about 20° to 100° C .If desired, non-interfering hydrophilic solvents other than water can be employed. Examples of such solvents are tetrahydrofuran, $CH_3CN$, and the like. Reaction times on the order of 0.1 to 24 hours, usually 0.5 to 4 hours, can be employed.

The methionine hydroxy analog or derivative product of the Reaction (3) can be recovered from the reaction medium in a conventional manner. For example, the reaction product can be recovered by crystallization of the MHA.

The above reaction scheme comprising reactions (1) to (3) provides a simple and straightforward system for producing methionine hydroxy analog or derivative using acrolein as the starting material. As can be seen, it totally avoids the use of deleterious HCN and the production of unwanted by-product ammonium sulfate.

The following examples are merely illustrative and are not to be considered as limiting.

EXAMPLE 1

Potassium acetate (12 g., 0.12 mol) was added to a solution of $CH_3SCH_2CH_2CHO$ (108.2 g, 1.04 mol) in acetic anhydride (153.4 g; 1.50 mol). The solution was heated to 145° C. for 3 hours. The amber-colored reaction mixture was cooled to room temperature, dissolved in 200 mL of pentane, washed with three 300 mL portions of $H_2O$, and stirred for 1 hour over 300 mL of saturated aqueous $NaHCO_3$ solution. After drying ($MgSO_4$), the product mixture was distilled at reduced pressure. The enol acetate, 1-acetoxy-3-methylthiopropene, was collected as a clear, colorless oil, bp 84°–90°/10 mm (105 g,), a 43:57 mixture of Z and E isomers, as determined by gas chromatographic analysis. The remainder of the product was 1, 1-diacetoxy-3-methylthiopropane (22g). The isolated yield of the mixture of the Z and E isomers was 72 percent. Small samples of the Z and E mixture were collected by preparative gas chromatography for the analysis, which was by gas chromatography, nmr, and infra-red spectroscopy.

EXAMPLE 2

47.9 mmoles of 3-(methylthio)propionaldehyde and 81.8 mmole of acetic anhydride, together with 6 mmoles of a catalyst comprising KOAc, and 5 mmoles of m-xylene internal standard were charged into a reaction vessel and heated to a temperature of 137° C. for 3.5 hours. The reaction was monitored quantitatively by gas chromatography. It was found that the conversion of the aldehyde was 80.9 percent, with a selectivity of 80.1 percent of the mixed Z and E isomers of 1-acetoxy-3-methylthiopropene and a selectivity of 17.3 percent for the diacetoxy compound mentioned in Example 1, with a Z/E isomer ratio of 41/59.

EXAMPLE 3

49.5 mmoles of 3-(methylthio)propionaldehyde and 76.8 mmole of acetic anhydride together with 6 mmoles of a catalyst comprising KOH, and 5 mmol of the m-xylene internal standard were charged into a reaction vessel and heated to a temperature of 140° C. for 3.5 hours. The reaction was monitored quantitatively by gas chromatography. It was found the the conversion of the aldehyde was 78.3 percent, with a selectivity of 75.2 percent of the mixed Z and E isomers of 1-acetoxy-3-methylthiopropene and a selectivity of 18.6 percent for the diacetoxy compound mentioned in the Example 1, with a Z/E isomer ration of 41/59.

EXAMPLE 4

43.7 mmoles of 3-(methylthio)propionaldehyde and 48.3 mmole of acetic anhydride together with 6 mmoles of a catalyst comprising pyridine, and 5 mmol of m-xylene internal standard were charged into a reaction vessel and heated to a temperature of 134° C. for 4 hours. The reaction was monitored quantitatively by gas chromatography. It was found that the conversion of the aldehyde was 75.6 percent, with a selectivity of 74.4 percent of the mixed Z and E isomers of 1-acetoxy-3-methylthiopropene and a selectivity of 24.2 percent for the diacetoxy compound mentioned in Example 1 with a Z/E isomer ratio of 38/62.

EXAMPLE 5

48.2 mmoles of 3-(methylthio)propionaldehyde and 53 mmole of acetic anhydride together with 2.5 mmoles of a catalyst comprising sodium benzoate, and 5 mmol of m-xylene internal standard were charged into a reaction vessel and heated to a temperature of 133° C. for 4 hours. The reaction was monitored quantitatively by gas chromatography. It was found that the conversion of the aldehyde was 87.2 mol percent, with a selectivity of 58.0 percent of the mixed Z and E isomers of 1-acetoxy-3-methylthiopropene and a selectivity of 21.1 percent for the diacetoxy compound mentioned in Example 1, with a Z/E isomer ratio of 39/61.

EXAMPLE 6

50 mmoles of 3-(methylthio)propionaldehyde and 75 mmole of acetic anhydride together with 6 mmoles of a catalyst comprising triethylamine, and 5 mmol of m-xylene internal standard were charged into a reaction vessel and heated to a temperature of 138° C. for 4 hours. The reaction was monitored quantitatively by gas chromatography. It was found that the conversion of the aldehyde was 88.2 percent, with a selectivity of 65.8 percent of the mixed Z and E isomers of 1-acetoxy-3-methylthiopropene and a selectivity of 9.1 percent for the diacetoxy compound mentioned in Example 1, with a Z/E isomer ratio of 38/62.

EXAMPLE 7

50 mmoles of 3-(methylthio)propionaldehyde and 50 mmole of acetic anhydride together with 6 mmoles of a catalyst comprising triphenyl phosphine, and 5 mmol of m-xylene internal standard were charged into a reaction vessel and heated to a temperature of 130° C. for 3 hours. After 70 minutes of the 3 hours 26.4 more mmoles of triphenyl phosphine were added. The reaction was monitored quantitatively by gas chromatography. It was found that the yield of the mixed Z and E isomers of 1-acetoxy-3-methylthiopropene was 14.1 mmoles and the yield of the diacetoxy compound mentioned in Example 1 was 2.3 mmoles with a Z/E isomer ratio of 41/59.

EXAMPLE 8

45.6 mmoles of 3-(methylthio)propionaldehyde and 51.5 mmole of acetic anhydride together with 6 mmoles of a catalyst comprising RbOAc, and 5 mmol of m-xylene intennal standard were charged into a reaction vessel and heated to a temperature of 131° C. for 4.5 hours. The reaction was monitored quantitatively by gas chromatography. It was found that the conversion of the aldehyde was 87.6 percent, with a selectivity of 65.7 percent of the mixed Z and E isomers of 1-acetoxy-3-methylthiopropene and a selectivity of 13.9 percent for the diacetoxy compound mentioned in Example 1, with a Z/E isomer ratio of 42/58.

EXAMPLE 9

45.4 mmoles of 3-(methylthio)propionaldehyde and 51.7 mmole of acetic anhydride together with 10.6 mmoles of a catalyst comprising HOAc, and 5 mmol of m-xylene internal standard were charged into a reaction vessel and heated to a temperature of 135° C. for 8 hours. The reaction was monitored quantitatively by gas chromatography. It was found that the conversion of the aldehyde was 56.4 percent, with a selectivity of 55.7 percent of the mixed Z and E isomers of 1-acetoxy-3-methylthiopropene and a selectivity of 38.9 percent isomer ratio of 63/37.

EXAMPLE 10

40.5 mmoles of 3-(methylthio)propionaldehyde and 47.4 mmole of acetic anhydride together with 0.5 mmoles of a internal standard were charged into a reaction vessel and heated to a temperature of 135° C. for 5 hours. The catalyst was insoluble. The reaction was monitored quantitatively by gas chromatography. It was found that the conversion of the aldehyde was 35.3 mol percent, with a selectivity of 24.5 percent of the mixed -Z and E isomers of 1-acetoxy-3-methylthiopropene and a selectivity of 25.9 percent for the diacetoxy compound mentioned in Example 1, with a Z/E isomer ratio of 51/49.

EXAMPLE 11

48.2 mmoles of 3-(methylthio)propionaldehyde and 39.7 mmole of propionic anhydride together with 6 mmoles of a catalyst comprising KOAc, and 5 mmol of m-xylene internal standard were charged into a reaction vessel and heated to a temperature of 135° C. for 4 hours. The catalyst was insoluble. The reaction was monitored quantitatively by gas chromatography. It was found that the conversion of the aldehyde gas 86.4 mol percent. Substantially, the only products formed were 1-propionyloxy-3-methylthiopropene, as the mixed Z and E isomers, plus 1,1'-dipropionyloxy-3-methylthiopropane, with the majority being the former. The products were identified by gas chromatograpy and mass spectroscopy.

EXAMPLE 12

11.6 mmoles of 3-(methylthio)propionadehyde and 8.3 mmole of acetic anhydride together with 1mmole of a catalyst comprising KOAc, and 5 mmol of m-xylene internal standard were dissolved in 2.5 ml of diethylene alycol dimethyl ether and charged into a reaction vessel and heated to a temperature of 100° C. for 6 hours. The reaction was monitored quantitatively by gas chromatography. It was found that the conversion of the aldehyde was 57.8 mol percent, with a selectivity of 100 percent of the mixed Z and E isomers of 1-acetoxy-3-methylthiopropene and with no diacetoxy compound being formed.

EXAMPLE 13

A mixture of 0.1 moles of 3-(methylthio)propionaldehyde and 0.15 moles of isopropenyl acetate together with 200 mg. of p-toluenesulfonic acid as catalyst was heated to reflux (90° C.) with stirring for 24 hours. Gas chromatographic analysis at the end of this time showed four components in addition to unreacted isopropenyl acetate and acetone. Treatment of Et$_2$O solution of the crude product mixture with aqueous NaHCO$_3$ solution and drying over an MgSO$_4$-activated charcoal mixture removed the allylidene diacetate. The products were distilled at reduced pressure.

| Component | Peak Area (% of total) |
| --- | --- |
| (1) CH$_2$=CHCH(O$_2$CCH$_3$)$_2$ | 46.4% |
| (2) Z-CH$_3$SCH$_2$CH=CHO$_2$CCH$_3$ | 18.6% |
| (3) E-CH$_3$SCH$_2$CH=CHO$_2$CCH$_3$ | 11.7% |
| (4) CH$_3$SCH$_2$CH$_2$CH(O$_2$CCH$_3$)$_2$ | 23.3% |

EXAMPLE 14

Treatment of a solution of CH$_3$SCH$_2$CH$_2$CHO (0.10 mol) in 45 ml of dry pyridine with acetyl chloride (0.20 mol) at 90° C., followed by aqueous wash and Et$_2$O extraction, gave approximately 1 g of oil whose GC showed presence of the enol acetate and the 1,1-diacetate

EXAMPLE 15

0.5 mmoles 1-acetoxy-3-methylthiopropene (Z:E ratio 43:57) and 2.5 mmoles methanol were charged into a 71 cc stainless steel bomb equipped with a glass liner and a Teflon coated stir bar. Ten mole percent, based on 1-acetoxy-3-methylthiopropene, of a catalyst comprising bis(triphenylphosphine)dichloropalladium, ($\phi_3$P)$_2$PdCl$_2$, was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 92.5 hours with stirring. At the termination of the reaction, the reaction products were analyzed by gas chromatography and it was found that 2-acetoxy-4-(methylthio)butanoic acid, methyl ester was produced in a yield of 28.6 percent and that 2-acetoxy-4-(methylthio)thiobutanoic acid, methyl ester was produced in a yield of 19.5 percent, based on the 1-acetoxy-3-methylthiopropene reactant charged. Note that each of the products is hydrolyzable to methionine hydroxy analog.

EXAMPLE 16

0.5 mmoles 1-acetoxy-3-methylthiopropene (Z:E ratio 43:57) and 2.5 mmoles 2-propanol were charged into a 71 cc stainless steel bomb equipped with a glass liner and a Teflon coated stir bar. No catalyst was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that no 2-acetoxy-4-(methylthio)butanoic acid, 2-propyl ester was produced and that no 2-acetoxy-4-(methylthio)thiobutanoic acid, methyl ester was produced. 0.0515 mmoles of acrolein and 0.0456 mmoles of methyl acetate were the only products detectable.

EXAMPLE 17

0.5 mmoles 1-acetoxy-3-methylthiopropene, pure E isomer, and 2.5 mmoles methanol were charged into a 71 cc stainless steel bomb equipped with a glass liner and a Teflon coated stir bar. No catalyst was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that no 2-acetoxy-4-(methylthio)butanoic acid, methyl ester was produced and that no 2-acetoxy-4-(methylthio)thiobutanoic acid, methyl ester was produced. 0.16 mmoles of acrolein and 0.0294 mmoles of $CH_3SCH_2H_2CHO$ were the only detectable products.

EXAMPLE 18

0.5 mmoles 1-acetoxy-3-methylthiopropene, pure Z isomer, and 2.5 mmoles methanol were charged into a 71 cc stainless steel bomb equipped with a glass liner and a Teflon coated stir bar. No catalyst was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that no 2-acetoxy-4-(methylthio)butanoic acid, methyl ester was produced and that no 2-acetoxy-4-(methylthio)thiobutanoic acid, methyl ester was produced. 0.15 mmoles of acrolein and 0.11 mmoles of methyl acetate, and 0.04 mmoles of $CH_3SCH_2CH_2CHO$ were the only detectable products.

EXAMPLE 19

0.5 mmoles 1-acetoxy-3-methylthiopropene (Z-:E ratio 43:57) and 0.5 mmoles methanol were charged into a 71 cc stainless steel bomb equipped with a glass liner and a Teflon coated stir bar. One mole percent, based on 1-acetoxy-3-methylthiopropene, of a catalyst comprising $Mn_2(CO)_{10}$ was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 120° C. and allowed to react for 44 hours with stirring. At the termination of the reaction, the reaction products were analyzed by gas chromatography and it was found that no 2-acetoxy-4-(methylthio)butanoic acid, methyl ester was produced and that no 2-acetoxy-4-(methylthio)thiobutanoic acid, methyl ester was produced.

EXAMPLE 20–31

Example 19 was repeated several times except that the following catalysts were used in separate experiments:

(20) $RuCl_2(P\phi_3)_3$
(21) $Ru_3(CO)_{12}$
(22) $RhCl_3$* +100 psi $H_2$
(23) $[Rh(CO)_2Cl]_2$
(24) $PtCl_2(1\%)+SnCl_2(1\%)+\phi_3As$ (2%)
(25) $NiCl_2$* +100 psi $H_2$
(26) $Ni(CO)_2(P\phi_3)_2$
(27) $Ni(OAc)_2+HI(2\%)$
(28) $ClIr(CO)(P\phi_3)_2$ Results were the same as reported for Example 19, i.e., no desired product was formed. *10 percent instead of 1 percent.

When $Fe(CO)_5(29)$; $Co_2(CO)_8(30)$; or $PtCl_2(31)$ were used to repeat Example 19 in place of $Mn_2(CO)_{10}$ catalyst, no 2-acetoxy-4-(methylthio)butanoic acid, methyl ester, was formed, but a small amount of the corresponding thiobutanoic acid ester formed.

All of the catalysts of Examples 20–31 are known catalysts for the hydrocarboxylation of alkenes, but are not effective in the present Reaction (2).

EXAMPLE 32

0.5 mmoles 1-acetoxy-3-methylthiopropene, (Z: E ratio 43:57), and 2.5 mmoles methanol were charged into a 71 cc stainless steel bomb equipped with a glass liner and a Teflon coated stir bar. No catalyst was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that no 2-acetoxy-4-(methylthio)- butanoic acid, methyl ester was produced, and that no 2-acetoxy-4-(methylthio)thiobutanoic acid, methyl ester was produced.

EXAMPLE 33

0.5 mmoles 1-acetoxy-3-methylthiopropene, (Z: E ratio 43:57), and 2.5 mmoles methanol were charged into a 71 cc stainless steel bomb equipped with a glass liner and a Teflon coated stir bar. A catalyst comprising $[Pd(CH_3CN)_4]^{+2}[BF_4]_2^-$ plus $P\phi_3$ was added. Toluene $LPd(CH3CN)4][BF4]2$ was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that 2-acetoxy-4-(methylthio)-butanoic acid, methyl ester was produced in a yield of 8.5 percent, and that 2-acetoxy-4-(methylthio)thiobutanoic acid, methyl ester was produced in a yield of 24.6 percent, based on the 1-acetoxy-3-methylthiopropene reactant charged. Note that each of the products is hydrolyzable to methionine hydroxy analog.

EXAMPLE 34

0.5 mmoles 1-acetoxy-3-methylthiopropene, (Z: E ratio 43:57), and 2.5 mmoles methanol were charged into a 71 cc stainless steel bomb equipped with a glass liner and a Teflon coated stir bar. Ten mole percent, based on 1-acetoxy-3-methylthiopropene, of a catalyst comprising $Pd(P\phi_3)_4$ plus 10 mole percent HCl co-catalyst was added. Toluene was included as an internal standard Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 45.25 hours with stirring. At the termination of the reaction, the reaction products were analyzed by gas chromatography and it was found that 2-acetoxy-4-(methylthio)butanoic acid, methyl ester was produced in a yield of 21.7 percent, and that 2-acetoxy-4-(methylthio)-thiobutanoic acid, methyl ester was produced in a yield of 17.8 percent, based on the 1-acetoxy-3-methylthiopropene reactant charged. Note that each of the products is hydrolyzable to methionine hydroxy analog. When this run was repeated without the HCl co-catalyst (run length 44 hours), the yields of the above ester and thioester were3 93 percent.and 4.48 percent, respectively.

EXAMPLE 35

0.5 mmoles 1-acetoxy-3-methylthiopropene, (Z: E ratio 43:5.7), and 10 mmoles methanol were charged into a 71 cc stainless steel bomb equipped with a glass liner and a Teflon coated.stir bar. Ten mole percent, based on 1-acetoxy-3-methylthiopropene, of a catalyst comprising bis(triphenylphosphine)dichloropalladium, $(\phi_3P)_2PdCl_2$, was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that 2-acetoxy-4-(methylthio)butanoic acid, methyl ester was produced in a yield of 28.6 percent, and that 2-acetoxy-4-(methylthio)thiobutanoic acid, methyl ester was produced in a yield of 16.8 percent, based on the 1-acetoxy-3-methylth.lopropene reactant charged. Note that each of the products is hydrolyzable to methionine hydroxy analog.

EXAMPLE 36

0.5 mmoles 1-acetoxy-3-methylthiopropene, (Z: E ratio 43:57), and 2.5 mmoles ethanol were charged into a 71 cc stainless steel bomb equipped with a glass liner and a Teflon coated stir bar. Ten mole percent, based on 1-acetoxy-3-methylthiopropene, of a catalyst comprising bis(triphenylphosphine)dichloropalladium, $(\phi_3P)_2PdCl_2$, was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that 2-acetoxy-4-(methylthio)butanoic acid, ethyl ester was produced in a yield of 10.5 percent, and that 2-acetoxy-4-(methylthio)thiobutanoic acid, methyl ester, was produced in a yield of 10.8 percent, based on the 1-acetoxy-3-methylthiopropene reactant charged. Note that each of the products is hydrolyzable to methionine hydroxy analog.

EXAMPLE 37

0.5 mmoles 1-acetoxy-3-methylthiopropene, (Z: E ratio 43:57), and 2.5 mmoles 2-propanol were charged into a 71 cc stainless steel bomb equipped with a glass liner and a Teflon coated stir bar. Ten mole percent, based on 1-acetoxy-3-methylthiopropene, of a catalyst comprising bis(triphenylphosphine)dichloropalladium, $(\phi_3P)_2PdCl_2$, was added. Toluene was included as an internal standard Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that 2-acetoxy-4-(methylthio)butanoic acid, 2-propyl ester was produced in a yield of 4.7 percent, and that 2-acetoxy-4-(methylthio)-thiobutanoic acid, methyl ester was produced in a yield of 10.1 percent, based on the 1-acetoxy-3-methylthiopropene reactant charged. Note that each of the products is hydrolyzable to methionine hydroxy analog.

EXAMPLE 38

0.5 mmoles 1-acetoxy-3-methylthiopropene, (Z: E ratio 43:57), and 2.5 mmoles methyl mercaptan were charged into a 71 cc stainless steel bomb equipped with a glass liner and a Teflon coated stir bar. Ten mole percent, based on 1-acetoxy-3-methylthiopropene, of a catalyst comprising bis(triphenylphosphine)dichloropalladium, $(\phi_3P)_2PdCl_2$, was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that a small amount of 2-acetoxy-4-(methylthio) thiobutanoic acid, methyl ester was produced. Previously, this new thio compound from a number of runs similar to Example 15 were isolated by preparative gas chromatography and identified by mass spectroscopy and gas chromatography, as well as by infrared spectroscopy.

EXAMPLE 39

410 mg (2.0) mmoles) 2-acetoxy-4-(methylthio)-butanoic acid, methyl ester in 10 cc 2N aqueous HCl was maintained at a temperature of about 50° C. for 4 hours with stirring. The reaction system was cooled to room temperature and extracted twice with 25 ml aliquots of ethyl ether. The ethyl ether layer was then dried with magnesium sulfate which was filtered off. Then the ether was evaporated from the dried ether solution, leaving a yellow oil product which was analyzed by proton nmr and determined to be composed of 300 mg (representing a 92 percent yield) methionine hydroxy analog. This analysis was confirmed by gas chromatography.

EXAMPLE 40

0.5 mmoles 1-acetoxy-3-methylthiopropene, (Z: E ratio 43:57), and 0.5 mmoles methanol were charged into a 71 cc stainless steel bomb equipped with a glass liner and a Teflon coated stir bar. Ten mole percent, based on 1-acetoxy-3methylthiopropene, of a catalyst comprising [(allyl)PdCl]$_2$ plus P$\phi_3$ co-catalyst (200 mole percent) was added. Toluene was included as an internal standard. Five milliliters of tetrahydrofuran as a solvent were also included in the reaction system. The reaction mixture was charged under argon. The bomb was sealed and carbon monoxide at a pressure of 500 psi (at room temperature) was charged to the bomb, and the bomb was heaterd to 100° C. and allowed to react for 44 hours with stirring. At the termination of the reaction, the reaction produrts were analyzed by gas chromatography and it was found that 2-acetoxy-4-(methylthio)butanoic acid, methyl ester was produced in a yield of 1.5 percent, and that 2-acetoxy-4-(methylthio)-thiobutanoic acid, methyl ester was produced in a yield of 3 percent, based on the 1-acetoxy-3-methylthiopropene reactant charged. Each of the products is hydrolyzable to methionine hydroxy analog.

EXAMPLE 41

0.5 mmoles 1-acetoxy-3-methylthiopropene, (Z:E ratio 43:57) and 2.5 mmoles methanol were charged into a 71 cc stainless steel. bomb equipped with a glass liner and a Teflon coated stir bar. Ten mole percent, based on 1-acetoxy-3methythiopropene, of a catalyst comprising bis(triphenylphosphine)dichloropalladium, ($\phi_3$P)$_2$PdCl$_2$, was added. Toluene was included as an internal standard. Five milliliters of benzene as a solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours with stirring. At the termination of the reaction, the reaction products were analyzed by gas chromatography and it was found that 2-acetoxy-4-(methylthio)-butanoic acid, methyl ester was produced in a yield of 22 percent, and that 2-acetoxy-4-(methylthio)thiobutanoic acid, methyl ester was produced in a yield of 10 percent, based on the 1-acetoxy-3-methylthiopropene reactant charged. Each of the products is hydrolyzable to methionine hydroxy analog.

EXAMPLE 42

0.5 mmoles 1-acetoxy-3-methylthiopropene, (Z:E ratio 43:57), and 2.5 mmoles methanol were charged into a 71 cc stainless steel bomb equipped with a glass liner and a Teflon coated stir bar. Ten mole percent, based on 1-acetoxy-3-methylthiopropene, of a catalyst comprising bis(triphenylphosphine)dichloropalladium, ($\phi_3$P)$_2$PdCl$_2$, was added. Toluene was included as an internal standard. Five milliliters of CH$_3$CN as a solvent were also included in the reaction system. The reaction mixture was charged under argon. The bomb was sealed and carbon monoxide at a pressure of 500 psi (at room temperature) was charged to the bomb, and the bomb was heated to 120° C. and allowed to react for 44 hours with stirring. At the termination of the reaction, the reaction products were analyzed by gas chromatography and it was found that 2-acetoxy-4-(methylthio)-butanoic acid, methyl ester was produced in a yield of 3 percent, and that 2-acetoxy-4-(methylthio)thiobutanoic acid, methyl ester was produced in a yield of 10 percent, based on the 1-acetoxy-3-methylthiopropene reactant charged. Each of the products is hydrolyzable to methionine hydroxy analog.

EXAMPLE 43

0.5 mmoles 1-acetoxy-3-methylthiopropene, (Z:-E ratio 43:57), and 2.5 mmoles methanol were charged into a 71 cc stainless steel bomb equipped with a glass liner and a Teflon coated stir bar. Ten mole percent, based on 1-acetoxy-3-methylthiopropene, of a catalyst comprising bis(triphenylphosphine)dichloropalladium, ($\phi_3$P)$_2$PdCl$_2$, was added. Toluene was included as an internal standard. Five milliliters of tetrahydrofuran as a solvent were also included in the reaction system. The reaction mixture was charged under argon. The bomb was sealed and carbon monoxide at a pressure of 500 psi (at room temperature) was charged to the bomb, and the bomb was heated to 100° C. and allowed to react for 44 hours with stirring. At the termination of the reaction, the reaction products were analyzed by gas chromatography and it was found that 2-acetoxy-4-(methylthio)butanoic acid, methyl ester was produced in a yield of 12.4 percent based on the 1-acetoxy-3-methylthiopropene reactant charged. 2-acetoxy -4-(methylthio)thiobutanoic acid, methyl ester was recovered in a yield of 8.7 percent.

EXAMPLE 44

0.5 mmoles 1-acetoxy-3-methylthiopropene, (Z:E ratio 43:57), and 2.5 mmoles methanol were charged into a 71 cc stainless steel bomb equipped with a glass liner and a Teflon coated stir bar. One mole percent, based on 1-acetoxy-3-methylthiopropene, of a catalyst comprising bis(triphenylphosphine)dichloropalladium, ($\phi_3$P)$_2$PdCl$_2$, was added. Toluene was included as an internal standard. Five milliliters of tetrahydrofuran as a solvent were also included in the reaction system. The reaction mixture was charged under argon. The bomb was sealed and carbon monoxide at a pressure of 1000 psi (at room temperature) was charged to the bomb, and the bomb was heated to 120° C. and allowed to react for 44 hours with stirring. At the termination of the reaction, the reaction products were analyzed by gas chromatography and it was found that 2-acetoxy-4-(methylthio)butanoic acid, methyl ester was produced in a yield of 17 percent and that 2-acetoxy-4-(methylthio)thiobutanoic acid, methyl ester was produced in a yield of 12.3 percent, based on the 1-acetoxy-3-methylthiopropene reactant charged. Each of the products is hydrolyzable to methionine hydroxy analog.

EXAMPLES 45–49

In each run about 0.5 mmoles 1-acetoxy-3-methylthiopropene and 2.5 mmoles methanol were charged into a 71 cc stainless steel bomb equipped with a glass liner and a Teflon coated stir bar. One mole percent, based on 1-acetoxy-3-methylthiopropene, of a catalyst comprising bis(triphenylphosphine) dichloropalladium, ($\phi_3$P)$_2$PdCl$_2$, was added. Toluene was included as an internal standard. Five milliliters of the indicated solvent were also included in the reaction system. The reaction mixture was charged under argon. The bomb was sealed and carbon monoxide at a pressure of 1000 psi (at room temperature) was charged to the bomb, and the bomb was heated to 100° C. and allowed to react for 44 hours. Various ratios of the enol acetate isomers were used as starting material, as shown. At the termination of the reaction, the reaction products were analyzed by gas chromatography and the yields of 2-acetoxy-4-(methylthio)butanoic acid, methyl ester (1) and 2-acetoxy-4-(methylthio)thiobutanoic acid, methyl ester (2), based on the 1-acetoxy-3-methylthiopropene reactant charged, were as shown in the table below. Shown also are the conversion of Z and E isomers and their percent conversions.

| Run No. | Solvent | Starting Mat. mmoles Z | Starting Mat. mmoles E | Conversion mmoles Z | Conversion mmoles E | Conversion Percent Z | Conversion Percent E | Yields (1) | Yields (2) |
| --- | --- | --- | --- | --- | --- | --- | --- | --- | --- |
| 45 | THF | 0.213 | 0.243 | 0.163 | 0.217 | 76.5 | 89.3 | 29.2 | 13.2 |
| 46 | THF | 0.53 | 0.022 | 0.441 | 0 | 83.2 | 0 | 26.8 | 8.0 |
| 47 | THF | 0.01 | 0.542 | * | 0.444 | * | 82.0 | 31.2 | 8.2 |
| 48 | benzene | 0.212 | 0.260 | 0.165 | 0.244 | 78.1 | 86.1 | 23.3 | 10.6 |
| 49 | benzene | 0.01 | 0.542 | * | 0.397 | * | 73.2 | 20.5 | 4.6 |

* not measured

As will be evident to those skilled in the art, various modifications of this invention can be made or followed in the light of the foregoing disclosure and discussion without departing from the spirit and scope of the disclosure or from the scope of the claims.

We claim:
1. 1-acetoxy-3-methylthiopropene.
2. 1-propionyloxy-3-methylthiopropene.
3. 2-acetoxy-4-(methylthio)thiobutanoic acid, methyl ester.

* * * * *